(12) United States Patent
Kehler et al.

(10) Patent No.: US 10,030,007 B2
(45) Date of Patent: *Jul. 24, 2018

(54) QUINAZOLIN-THF-AMINES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Morten Langgård, Glostrup (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,104

(22) Filed: Jun. 5, 2017

(65) Prior Publication Data

US 2017/0267664 A1 Sep. 21, 2017

Related U.S. Application Data

(63) Continuation of application No. 15/105,647, filed as application No. PCT/EP2014/078475 on Dec. 18, 2014, now Pat. No. 9,701,665.

(30) Foreign Application Priority Data

Dec. 19, 2013 (DK) .................................. 2013 00707
May 6, 2014 (DK) .................................. 2014 00249

(51) Int. Cl.
  *C07D 405/12* (2006.01)
(52) U.S. Cl.
  CPC .................................. *C07D 405/12* (2013.01)

(58) Field of Classification Search
  CPC .................................................... C07D 405/12
  See application file for complete search history.

(56) References Cited

U.S. PATENT DOCUMENTS 9,701,665 B2 *   7/2017   Kehler ................ C07D 405/12
2016/0318910 A1   11/2016   Kehler et al.

FOREIGN PATENT DOCUMENTS

WO   WO 2007/022280   2/2007
WO   WO 2007/096743   8/2007

OTHER PUBLICATIONS

International Search Report PCT/EP2014/078475 (WO 2015/091805) (2015) (2 pages).
Lack, N. A. et al. (2011) "Targeting the Binding Function 3 (BF3) Site of the Human Androgen Receptor Through Virtual Screening," J. Medicinal Chem. 54:8563-8573.
STN CASplus Entry for Lack (obtained from STN on Mar. 10, 2016).
Written Opinion of the International Searching Authority PCT/EP2014/078475 (WO 2015/091805) (2015) (4 pages).

* cited by examiner

*Primary Examiner* — James D. Anderson
(74) *Attorney, Agent, or Firm* — Wolf, Greenfield & Sacks, P.C.

(57) ABSTRACT

The present invention provides Quinazolin-THF-amines as PDE I inhibitors and their use as a medicament, in particular for the treatment of neurodegenerative disorders and psychiatric disorders.

11 Claims, No Drawings

QUINAZOLIN-THF-AMINES AS PDE1 INHIBITORS

CROSS-REFERENCE TO RELATED APPLICATIONS

This application is a continuation of U.S. patent application Ser. No. 15/105,647 (filed on Jun. 17, 2016; pending), which application is a § 371 application of PCT Application No. PCT/EP2014/078475 (filed on Dec. 18, 2014; now expired), which claims priority to Danish Patent Applications No.: PA 2013 00707 (filed on Dec. 19, 2013) and PA 2014 00249 (filed on May 6, 2014), each of which applications is herein incorporated by reference in its entirety.

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of concentrations in all cells, and their varied regulatory mechanisms provide for integration and crosstalk with myriad signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91:651-690).

On the basis of substrate specificity, the POE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is Ca2+-dependently regulated via calmodulin (CaM, a 16 kDa Ca2+-binding protein) complexed with four Ca2+(for review, Sharron H. Francis, Mitsi A. Blount, and Jackie D. Corbin. Physiol Rev 2011, 91: 651-690). Thus, this family represents an interesting regulatory link between cyclic nucleotides and intracellular Ca2+. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two Ca2+/CaM binding domains and two phosphorylation sites differentiate their corresponding proteins and modulate their biochemical functions. PDE1 is a dual substrate PDE and the PDE1 C-subtype has equal activity towards cAMP and cGMP (Km≈1-3 μM), whereas the subtypes PDE1A and PDE1 B has a preference for cGMP (Km for cGMP≈1-3 μM and for cAMP≈10-30 μM).

The PDE1 subtypes are highly enriched in the brain and located especially in the striatum (PDE1 B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 Feb. 21) have suggested the potential for the therapeutic use of PDE1 inhibitors in neurological disorders, like e.g. Alzheimer's, Parkinson's and Huntington's Diseases and in psychiatric disorders like e.g. Attention Deficit hyperactivity Disorder (ADHD), restless leg syndrome, depression, narcolepsy, cognitive impairment and cognitive impairment associated with schizophrenia (CIAS). There have also been patent applications claiming that PDE1 inhibitors are useful in diseases that may be alleviated by the enhancement of progesterone-signalling such as female sexual dysfunction.

The compounds of the invention may offer alternatives to current marketed treatments for neurodegenerative and/or psychiatric disorders, which are not efficacious in all patients. Hence, there remains a need for alternative methods of treatment.

SUMMARY OF THE INVENTION

PDE1 enzymes are expressed in the Central Nervous System (CNS), making this gene family an attractive source of new targets for the treatment of psychiatric and neurodegenerative disorders.

The objective of the present invention is to provide compounds that are PDE1 inhibitors, and as such are useful to treat neurodegenerative disorders and psychiatric disorders. In a preferred embodiment the compounds are selective PDE1 inhibitors.

Accordingly, the present invention relates to compounds of formula (I)

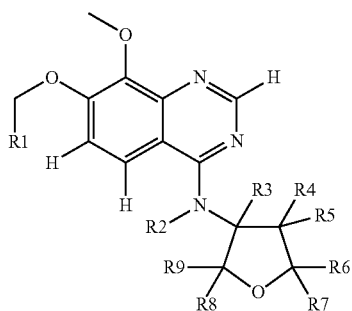

(I)

wherein
$R_1$ is selected from the group consisting of H and $C_1$ to $C_3$ alkyl;
$R_2$ is selected from the group consisting of H and $C_1$-$C_3$ alkyl, wherein the $C_1$-$C_3$ alkyl optionally is substituted one or more times with one or more substituents selected from the group consisting of phenyl and $C_3$-$C_6$ cycloalkyl,
$R_3$ is selected from the group consisting of H, methyl and ethyl,
$R_4$ is selected from the group consisting of H, hydroxy, methoxy and ethoxy,
$R_5$, $R_6$ and $R_7$ are H,
$R_8$ is selected from the group consisting of H, methyl, ethyl and cyclopropyl
$R_9$ is selected from the group consisting of H, methyl and ethyl
and pharmaceutically acceptable acid addition salts of Compound I, racemic mixtures of Compound I, or the corresponding enantiomer and/or optical isomer of Compound I, and polymorphic forms of Compound I as well as tautomeric forms of Compound I.

DETAILED DESCRIPTION OF THE INVENTION

Embodiments of the Invention

In a first embodiment (E1) the present invention relates to compounds of formula (I) (Compound I)

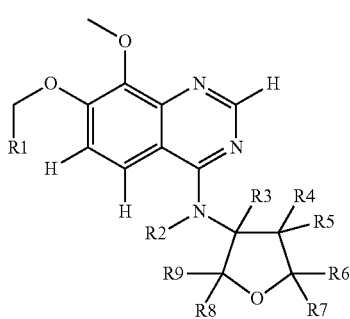

Compound (I)

wherein $R_1$ is selected from the group consisting of H and $C_1$-$C_3$ alkyl;
$R_2$ is selected from the group consisting of H and $C_1$-$C_3$ alkyl
wherein the $C_1$-$C_3$ alkyl optionally is substituted with phenyl or $C_3$-$C_6$ cycloalkyl;
$R_3$ is selected from the group consisting of H, methyl and ethyl
$R_4$ is selected from the group consisting of H, hydroxyl, methoxy and ethoxy and;
$R_5$, $R_6$ and $R_7$ are H
$R_8$ is selected from the group consisting of H, methyl, ethyl and cyclopropyl
$R_9$ is selected from the group consisting of H, methyl and ethyl
and pharmaceutically acceptable acid addition salts of Compound I, racemic mixtures of Compound I, or the corresponding enantiomer and/or optical isomer of Compound I, and polymorphic forms of Compound I as well as tautomeric forms of Compound I. In an embodiment (E2) of (E1) $R_2$ is H.

In an embodiment (E3) of (E1) $R_2$ is $CH_3$.
In an embodiment (E4) of (E3) $R_2$ is substituted with phenyl or cyclopropyl.
In an embodiment (E5) of (E1) $R_1$ is methyl.
In an embodiment (E6) of any of (E1) to (E5) the compound is a PDE1 inhibitor.
In an embodiment (E7) of any of (E1) to (E6) the compound is selected from the compounds of Table 1
In an embodiment (E8) of any of (E1) to (E7) the compound is for use as a medicament.
In an embodiment (E9) of any of (E1) to (E7) the compound is for use in treating ADHD, schizophrenia or cognitive impairment associated with schizophrenia.
Embodiment (E10) is the use of the compound of any of (E1) to (E7) for the manufacture of a medicament for the treatment of ADHD schizophrenia or cognitive impairment associated with schizophrenia.

Definitions

Pde1 Enzymes

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms.

Substituents

As used in the context of the present invention, the terms "halo" and "halogen" are used interchangeably and refer to fluorine, chlorine, bromine or iodine.

The terms "$C_1$-$C_3$ alkyl", "$C_1$-$C_4$ alkyl", "$C_1$-$C_5$ alkyl" and "$C_1$-$C_6$ alkyl" refer to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl.

The term "$C_3$-$C_6$ cycloalkyl" typically refers to cyclopropyl, cyclobutyl, cyclopentyl, and cyclohexyl.

The expression "alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "aryl" refers to a phenyl ring, optionally substituted with halogen, $C_1$-$C_6$ alkyl, $C_1$-$C_6$ alkoxy or halo($C_1$-$C_6$)alkyl as defined above.

The term "heteroaryl" monocyclic- or polycyclic aromatic ring comprising carbon atoms, hydrogen atoms, and one or more heteroatoms, preferably, 1 to 3 heteroatoms, independently selected from nitrogen, oxygen, and sulfur. Illustrative examples of heteroaryl groups include, but are not limited to, pyridinyl, pyridazinyl, triazinyl, pyrrolyl, pyrazolyl, imidazolyl, (1,2,3,)-triazolyl, (1,2,4)-triazolyl, pyrazinyl, pyrimidinyl, tetrazolyl, furanyl, thiophenyl, isoxazolyl, thiazolyl, isoxazolyl, and oxazolyl.

A heteroaryl group can be unsubstituted or substituted with one or two suitable substituents. Preferably, the heteroaryl of this invention is a monocyclic 5 or 6 membered heteroaryl, wherein the ring comprises 2 to 5 carbon atoms and 1 to 3 heteroatoms, referred to herein as "monocyclic 5 or 6 membered heteroaryl"

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

For example reference to the compound 7,8-dimethoxy-N-methyl-N-(tetrahydrofuran-3-yl)quinazolin-4-amine without any further specification covers (R)-7,8-dimethoxy-N-methyl-N-(tetrahydrofuran-3-yl)quinazolin-4-amine, (S)-7,8-dimethoxy-N-methyl-N-(tetrahydrofuran-3-yl)quinazolin-4-amine as well as mixtures of the enantiomers in any ratio, including the racemic mixture (±)7,8-dimethoxy-N-methyl-N-(tetrahydrofuran-3-yl)quinazolin-4-amine.

Correspondingly, reference to the compound 7,8-dimethoxy-N-(-2-methyltetrahydrofuran-3-yl)quinazolin-4-amine without any further specification covers all four covers all four stereoisomeric variants as well as mixtures thereof in any ratio, including the racemic mixture.

The above also applies where compounds of the invention contain more than two chiral centers.

Pde1 Inhibitors

In the context of the present invention a compound is considered to be a PDE1 inhibitor if the amount required to reach the $IC_{50}$ level of PDE1B is 5 micro molar or less, preferably less than 4 micro molar, such as 3 micro molar or less, more preferably 2 micro molar or less, such as 1 micro molar or less, in particular 500 nM or less. In preferred embodiments the required amount of PDE1 inhibitor required to to reach the $IC_{50}$ level of PDE1B is 400 nM or less, such as 300 nM or less, 200 nM or less, 100 nM or less, or even 80 nM or less, such as 50 nM or less, for example 25 nM or less.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Pharmaceutical Compositions

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising mixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described above.

For parenteral administration, solutions of the compounds of formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula (I) are PDE1 enzyme inhibitors and as such are useful to treat associated neurological and psychiatric disorders.

The invention thus provides a compound of formula (I) or a pharmaceutically acceptable acid addition salt thereof, as well as a pharmaceutical composition containing such a compound, for use in the treatment of a neurodegenerative disorder, psychiatric disorder or drug addiction in mammals including humans; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compounds of formula (I) or pharmaceutically acceptable salts thereof may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The present invention provides a method of treating a mammal, including a human, suffering from a neurodegenerative disorder selected from a cognition disorder or movement disorder, which method comprises administering to the subject a therapeutically effective amount of a compound of formula (I).

This invention further provides a method of treating a neurodegenerative disorder or condition in a mammal, including a human, which method comprises administering to said mammal an amount of a compound of formula (I) effective in inhibiting PDE1.

This invention also provides a method of treating a subject suffering from a psychiatric disorder, which method comprises administering to the subject a therapeutically effective amount of a compound of formula (I). Examples of psychiatric disorders that can be treated according to the present invention include, but are not limited to, Attention Deficit Hyperactivity Disorder (ADHD) schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

It has been found that the compounds of formula (I) or pharmaceutically acceptable salts thereof may advantageously be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The present invention thus provides a method of treating a mammal suffering from a psychiatric disorder, such as schizophrenia, which method comprises administering to the mammal a therapeutically effective amount of a compound of formula (I), either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The present invention further provides a method of treating a subject suffering from a cognition disorder, which method comprises administering to the subject a therapeutically effective amount of a compound of formula (I). Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder, which method comprises administering to the subject a therapeutically effective amount of a compound of formula (I). Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula (I).

This invention also provides a method of treating a mood disorder, which method comprises administering to the subject a therapeutically effective amount of a compound of formula (I). Examples of mood disorders and mood episodes that can be treated according to the present invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a disorder comprising as a symptom a deficiency in attention and/or cognition in a mammal, including a human, which method comprises administering to said mammal an amount of a compound of formula (I) effective in treating said disorder.

Other disorders that can be treated according to the present invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition involves neurodegeneration of striatal medium spiny neurons in a mammal, including a human.

In a further embodiment of the present invention, the neurodegenerative disorder or condition is Huntington's disease.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention; n.d. means "not determined"

| Compound number | Compound | PDE1C IC50 (nM) | PDE1B IC50 (nM) | PDE1A IC50 (nM) |
| --- | --- | --- | --- | --- |
| 1 | 7,8-Dimethoxy-N-(tetrahydrofuran-3-yl)quinazolin-4-amine | 590 | 230 | 1200 |
| 1 Stereoisomer 1 | 7,8-Dimethoxy-N-(tetrahydrofuran-3-yl)quinazolin-4-amine | 280 | 54 | 280 |
| 1 Stereoisomer 2 | 7,8-Dimethoxy-N-(tetrahydrofuran-3-yl)quinazolin-4-amine | 1200 | 600 | 1900 |
| 2 | trans-N-(-2-cyclopropyltetrahydrofuran-3-yl)-7,8-dimethoxyquinazolin-4-amine | 1300 | 260 | 2400 |
| 3 Stereoisomer 1 | 7,8-dimethoxy-N-(-2-methyltetrahydrofuran-3-yl)quinazolin-4-amine | 3000 | 1200 | 2500 |
| 3 Stereoisomer 2 | 7,8-dimethoxy-N-(-2-methyltetrahydrofuran-3-yl)quinazolin-4-amine | 310 | 94 | 490 |
| 3 Stereoisomer 3 | 7,8-dimethoxy-N-(-2-methyltetrahydrofuran-3-yl)quinazolin-4-amine | 390 | 100 | 890 |
| 3 Stereoisomer 4 | 7,8-dimethoxy-N-(-2-methyltetrahydrofuran-3-yl)quinazolin-4-amine | 270 | 120 | 580 |
| 4 | (7,8-dimethoxy-N-methyl-N-(tetrahydrofuran-3-yl)quinazolin-4-amine | 140 | 84 | 360 |
| 4 Stereoisomer 1 | (R)-7,8-dimethoxy-N-methyl-N-(tetrahydrofuran-3-yl)quinazolin-4-amine | 140 | 80 | 370 |
| 4 Stereoisomer 2 | (S)-7,8-dimethoxy-N-methyl-N-(tetrahydrofuran-3-yl)quinazolin-4-amine | 140 | 80 | 1400 |
| 5 | N-(2,3-dimethyltetrahydrofuran-3-yl)-7,8-dimethoxyquinazolin-4-amine | 130 | 33 | 130 |
| 5 Stereoisomer 1 | N-(2,3-dimethyltetrahydrofuran-3-yl)-7,8-dimethoxyquinazolin-4-amine | 1100 | 300 | 590 |
| 5 Stereoisomer 2 | N-(2,3-dimethyltetrahydrofuran-3-yl)-7,8-dimethoxyquinazolin-4-amine | 400 | 87 | 240 |
| 5 Stereoisomer 3 | N-(2,3-dimethyltetrahydrofuran-3-yl)-7,8-dimethoxyquinazolin-4-amine | 67 | 6 | 33 |
| 5 Stereoisomer 4 | N-(2,3-dimethyltetrahydrofuran-3-yl)-7,8-dimethoxyquinazolin-4-amine | 140 | 15 | 77 |
| 6 | 7,8-dimethoxy-N-(3-methyltetra-hydrofuran-3-yl)quinazolin-4-amine | 160 | 62 | 150 |

TABLE 1-continued

Compounds of the invention; n.d. means "not determined"

| Compound number | Compound | PDE1C IC50 (nM) | PDE1B IC50 (nM) | PDE1A IC50 (nM) |
|---|---|---|---|---|
| 6 Stereoisomer 1 | 7,8-dimethoxy-N-(3-methyltetra-hydrofuran-3-yl)quinazolin-4-amine | 400 | 110 | 290 |
| 6 Stereoisomer 2 | 7,8-dimethoxy-N-(3-methyltetra-hydrofuran-3-yl)quinazolin-4-amine | 110 | 37 | 140 |
| 7 | (S)-7,8-dimethoxy-N-(tetrahydrofuran-3-yl)quinazolin-4-amine | n.d. | n.d. | n.d. |
| 8 | (S)-N-ethyl-7,8-dimethoxy-N-(tetrahydrofuran-3-yl)quinazolin-4-amine | 510 | 250 | 480 |
| 9 | (S)-7,8-dimethoxy-N-propyl-N-(tetrahydrofuran-3-yl)quinazolin-4-amine | 540 | 180 | 280 |
| 10 | (S)-N-benzyl-7,8-dimethoxy-N-(tetrahydrofuran-3-yl)quinazolin-4-amine | 1400 | 360 | 820 |
| 11 | (S)-N-(cyclopropylmethyl)-7,8-dimethoxy-N-(tetrahydrofuran-3-yl)quinazolin-4-amine | 1600 | 420 | 850 |
| 12 | (R)-7,8-dimethoxy-N-(tetrahydrofuran-3-yl)quinazolin-4-amine | n.d. | n.d. | n.d. |
| 13 | (R)-N-ethyl-7,8-dimethoxy-N-(tetrahydrofuran-3-yl)quinazolin-4-amine | 1500 | 600 | 1200 |
| 14 | (R)-7,8-dimethoxy-N-propyl-N-(tetrahydrofuran-3-yl)quinazolin-4-amine | 360 | 180 | 270 |
| 15 | (R)-N-(cyclopropylmethyl)-7,8-dimethoxy-N-(tetrahydrofuran-3-yl)quinazolin-4-amine | 2100 | 820 | 2500 |
| 16 | (R)-N-benzyl-7,8-dimethoxy-N-(tetrahydrofuran-3-yl)quinazolin-4-amine | 1600 | 410 | 1200 |
| 17 | trans-7,8-dimethoxy-N-4-methoxytetrahydrofuran-3-yl)quinazolin-4-amine | 1300 | 520 | 2200 |
| 18 | trans-4-((7,8-dimethoxyquinazolin-4-yl)amino)tetrahydrofuran-3-ol | 2600 | 1300 | 2300 |
| 19 | cis-4-((7,8-dimethoxyquinazolin-4-yl)amino)tetrahydrofuran-3-ol | n.d. | 840 | 4600 |
| 20 Stereoisomer 1 | N-(2,3-Dimethyltetrahydrofuran-3-yl)-7,8-dimethoxy-N-methylquinazolin-4-amine | 33 | 5 | 19 |
| 20 Stereoisomer 2 | N-(2,3-Dimethyltetrahydrofuran-3-yl)-7,8-dimethoxy-N-methylquinazolin-4-amine | 27 | 4 | 26 |
| 20 Stereoisomer 3 | N-(2,3-Dimethyltetrahydrofuran-3-yl)-7,8-dimethoxy-N-methylquinazolin-4-amine | 890 | 190 | 440 |
| 20 Stereoisomer 4 | N-(2,3-Dimethyltetrahydrofuran-3-yl)-7,8-dimethoxy-N-methylquinazolin-4-amine | 170 | 39 | 120 |
| 21 Stereoisomer 1 | N-(2,2-dimethyltetrahydrofuran-3-yl)-7,8-dimethoxyquinazolin-4-amine | 2800 | 780 | 1500 |
| 21 Stereoisomer 2 | N-(2,2-dimethyltetrahydrofuran-3-yl)-7,8-dimethoxyquinazolin-4-amine | 1600 | 260 | 1300 |
| 22 Stereoisomer 1 | 7,8-dimethoxy-N-methyl-N-(2-methyltetrahydrofuran-3-yl)quinazolin-4-amine | 79 | 28 | 110 |
| 22 Stereoisomer 2 | 7,8-dimethoxy-N-methyl-N-(2-methyltetrahydrofuran-3-yl)quinazolin-4-amine | 55 | 35 | 210 |
| 22 Stereoisomer 3 | 7,8-dimethoxy-N-methyl-N-(2-methyltetrahydrofuran-3-yl)quinazolin-4-amine | 1500 | 430 | 1100 |
| 22 Stereoisomer 4 | 7,8-dimethoxy-N-methyl-N-(2-methyltetrahydrofuran-3-yl)quinazolin-4-amine | 780 | 1100 | 1500 |
| 23 Stereoisomer 1 | 7,8-dimethoxy-N-methyl-N-(3-methyltetrahydrofuran-3-yl)quinazolin-4-amine | 500 | 70 | 240 |
| 23 Stereoisomer 2 | 7,8-dimethoxy-N-methyl-N-(3-methyltetrahydrofuran-3-yl)quinazolin-4-amine | 170 | 55 | 160 |
| 24 | N-(3-Ethyltetrahydrofuran-3-yl)-7,8-dimethoxyquinazolin-4-amine | n.d. | n.d. | n.d. |
| 25 | N-(2-Cyclopropyltetrahydrofuran-3-yl)-7,8-dimethoxyquinazolin-4-amine | 1300 | 260 | 2400 |

EXPERIMENTAL SECTION

Preparation of the Compounds of the Invention
General Methods
Analytical LC-MS data were obtained using one of the methods identified below.
Method 1:
A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.
Method 2:
A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/min.
Method 3:
An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.
Method 4:
An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method 5:

An Agilent 1200 LCMS system with ELS detector was used. Column: XBridge ShieldRP18, 5 µm, 50×2.1 mm; Column temperature: 40° C.; Solvent system: A=water/NH$_3$*H2O (99.95:0.05) and B=acetonitrile; Method: Linear gradient elution with A:B=95:5 to 0:100 in 3.4 minutes and with a flow rate of 0.8 mL/min.

Method 6:

An Agilent 1200 LCMS system with ELS detector was used. Column: XBridge ShieldRP18, 5 µm, 50×2.1 mm; Column temperature: 40° C.; Solvent system: A=water/NH$_3$*H2O (99.95:0.05) and B=acetonitrile; Method: Linear gradient elution with A:B=99:1 to 0:100 in 3.4 minutes and with a flow rate of 0.8 mL/min.

Preparative LC-MS-purification was performed on a PE Sciex API 150EX instrument with atmospheric pressure chemical ionization. Column: 50×20 mm YMC ODS-A with 5 µm particle size; Solvent system: A=water/trifluoroacetic acid (99.965:0.035) and B=acetonitrile/water/trifluoroacetic acid (94.965:5:0.035); Method: Linear gradient elution with A:B=80:20 to 0:100 in 7 minutes and with a flow rate of 22.7 mL/minute. Fraction collection was performed by split-flow MS detection.

Preparative SFC was performed on a Thar 80 instrument. Exemplified conditions can be, but not limited to: Column AD 250×30 mm with 20 µm particle size; Column temperature: 38° C., Mobile phase: Supercritical CO$_2$/EtOH (0.2% NH$_3$H$_2$O)=45/55.

Example 1

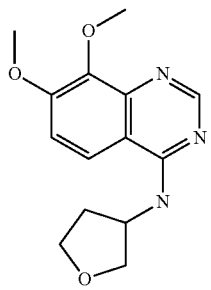 [SMILES: COc1ccc2c(NC3CCOC3)ncnc2c1OC]

7,8-Dimethoxy-N-(tetrahydrofuran-3-yl)quinazolin-4-amine

To a solution of 4-chloro-7,8-dimethoxyquinazoline (1.5 g, 6.7 mmol) in DMF (30 mL) was added tetrahydrofuran-3-amine (698 mg, 8.01 mmol), DIPEA (2.3 mL, 13 mmol). Nitrogen was bubbled through the mixture for 5 min. The reaction was then heated at 100° C. for 2 h. The crude mixture was evaporated and the residue was dissolved in ethyl acetate (20 mL), and filtered. The solid was washed with ethyl acetate (10 mL) to give 7,8-dimethoxy-N-(tetrahydrofuran-3-yl)quinazolin-4-amine 1.4 g (76%).

The racemate of 7,8-dimethoxy-N-(tetrahydrofuran-3-yl)quinazolin-4-amine 1.4 g was purified by SFC separation and numbered according to the order of elution:

Stereoisomer 1 (First Eluting by SFC): 388 mg, LC-MS (m/z) 276.1 (MH+) t$_R$ (minutes, method 3)=1.82. [α]$^{20}_D$=−32 (c=0.10 mg/mL, MeOH)

Stereoisomer 2 (Second Eluting by SFC): 413 mg LC-MS (m/z) 276.1 (MH+) t$_R$ (minutes, method 3)=1.81. [α]$^{20}_D$=23 (c=0.10 mg/mL, MeOH)

Example 2

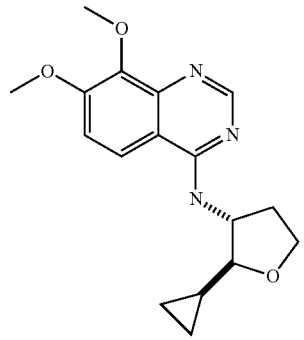

trans-N-(-2-cyclopropyltetrahydrofuran-3-yl)-7,8-dimethoxyquinazolin-4-amine

4-Chloro-7,8-dimethoxyquinazoline (200 mg, 0.890 mmol) and trans-2-cyclopropyl-tetrahydrofuran-3-amine (170 mg, 1.34 mmol) were mixed in isopropanol (10 ml) and DIPEA (230 mg, 0.311 ml, 1.78 mmol). The reaction was heated in a microwave reactor for 40 min at 160° C. After cooling to RT for a couple of hours a white precipitate was collected and dried overnight at 40° C. Further purified by flash chromatography using a gradient of ethyl acetate and heptane to yield trans-N-(-2-cyclopropyltetrahydrofuran-3-yl)-7,8-dimethoxyquinazolin-4-amine 80 mg (29%).

LC-MS (m/z) 316.0 (MH+), t$_R$ (minutes, method 2)=0.36.

Example 3

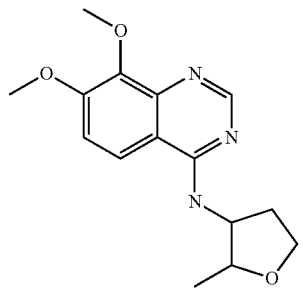 [SMILES: COc1ccc2c(NC3CCOC3C)ncnc2c1OC]

7,8-Dimethoxy-N-(-2-methyltetrahydrofuran-3-yl)quinazolin-4-amine

To a solution of 2-methyltetrahydrofuran-3-amine 2,2,2-trifluoroacetate (9.6 g, 45 mmol), 4-chloro-7,8-dimethoxyquinazoline (5.0 g, 22 mmol) in DMF (200 mL) was added DIPEA (14.4 g, 111 mmol). The mixture was stirred at 120° C. overnight. The mixture was concentrated and the residue purified by prep-HPLC to afford 1.2 g (19%) of 7,8-dimethoxy-N-(-2-methyltetrahydrofuran-3-yl)quinazolin-4-amine as a white solid.

A mixture of all possible stereoisomers of 7,8-dimethoxy-N-(-2-methyltetrahydrofuran-3-yl)quinazolin-4-amine (1.43 g, 4.90 mmol) was purified by SFC separation and numbered according to their order of elution:

Stereoisomer 1 (First Eluting by SFC): 213 mg, LC-MS (m/z) 290.1 (MH+).
$[\alpha]^{20}_D$=21 (c=0.1 mg/mL, MeOH)
Stereoisomer 2 (Second Eluting by SFC): 141 mg, LC-MS (m/z) 290.1 (MH+).
$[\alpha]^{20}_D$=−24 (c=0.1 mg/mL, MeOH)
Stereoisomer 3 (Third Eluting by SFC): 58 mg, LC-MS (m/z) 290.1 (MH+).
$[\alpha]^{20}_D$=65 (c=0.1 mg/mL, MeOH)
Stereoisomer 4 (Fourth Eluting by SFC): 132 mg, LC-MS (m/z) 290.1 (MH+).
$[\alpha]^{20}_D$=−54 (c=0.1 mg/mL, MeOH)

Example 4

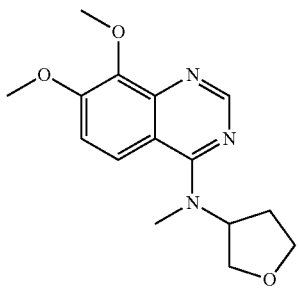 [SMILES: COc1ccc2c(N(C)C3CCOC3)ncnc2c1OC]

7,8-Dimethoxy-N-methyl-N-(tetrahydrofuran-3-yl)quinazolin-4-amine

4-Chloro 7,8-dimethoxyquinazoline (200 mg, 0.890 mmol) and N-methyltetrahydrofuran-3-amine (180 mg, 1.78 mmol) were mixed in isopropanol (10 ml) and DIPEA (575 mg, 0.78 ml, 4.5 mmol). The mixture was heated in a microwave oven for 30 min at 150° C. The reaction mixture was poured into H$_2$O (20 mL), extracted with ethyl acetate (3×20 mL), the combined organic phases were washed with brine, dried over MgSO$_4$ and concentrated in vacuo. The crude product was purified by flash chromatography using a gradient of ethyl acetate and ethyl acetate+5% methanol to yield 7,8-dimethoxy-N-methyl-N-(tetrahydrofuran-3-yl)quinazolin-4-amine 140 mg (54%).

LC-MS (m/z) 290.3 (MH+), $t_R$ (minutes, method 1)=0.34.
Stereoisomer 1

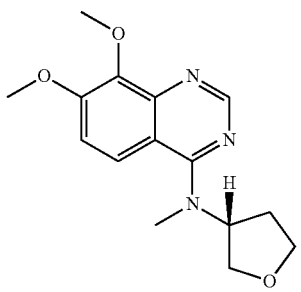 [SMILES: COc1ccc2c(N(C)[C@@H]3CCOC3)ncnc2c1OC]

(R)-7,8-dimethoxy-N-methyl-N-(tetrahydrofuran-3-yl)quinazolin-4-amine

To a solution of (R)-7,8-dimethoxy-N-(tetrahydrofuran-3-yl)quinazolin-4-amine (390 mg, 1.42 mmol) in THF (20 mL) was added NaH (283 mg, 7.08 mmol, 60%) at 0° C., and the mixture was stirred at 0° C. for 10 min. To the solution was added methyl iodide (1.0 g, 7.1 mmol) at 00° C. The reaction was allowed to warm 20° C. and stirred for 2 hours. The solution was quenched with sat. aq. NH$_4$Cl (0.3 mL), and concentrated under vacuum. The residue was diluted with ethyl acetate (50 mL), washed with brine, dried and concentrated under vacuum. The residue was purified by flash chromatography on silica gel (ethyl acetate/petroleum ether=1/10 to 2/1) to give (R)-7,8-dimethoxy-N-methyl-N-(tetrahydrofuran-3-yl)quinazolin-4-amine 400 mg (97%) as a white solid LC-MS (m/z) 290.1 (MH+), $t_R$ (minutes, method 6)=1.753.
$[\alpha]^{20}_D$=19 (c=0.1 mg/mL, CHCl$_3$)
Stereoisomer 2

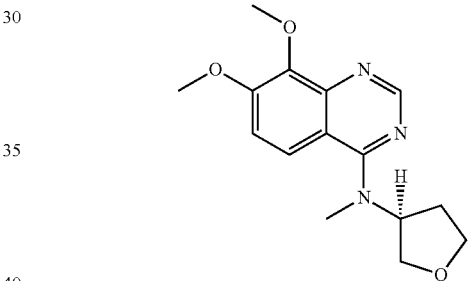

(S)-7,8-dimethoxy-N-methyl-N-(tetrahydrofuran-3-yl)quinazolin-4-amine

To a solution of (R)-7,8-dimethoxy-N-(tetrahydrofuran-3-yl)quinazolin-4-amine (420 mg, 1.52 mmol) in THF (20 mL) was added NaH (305 mg, 7.63 mmol, 60%) at 0° C. The reaction was stirred at 0° C. for 10 min. Methyl iodide (1.08 g, 7.63 mmol) was added at 0° C. and the mixture allowed to warm to 20° C. and stirred for 2 hours. The solution was quenched with sat. aq. NH$_4$Cl (0.3 mL), and concentrated under vacuum. The residue was diluted with ethyl acetate (50 mL), washed with brine, dried and concentrated under vacuum. The residue was purified by flash chromatography on silica gel (eluted ethylacetate/petroleum ether=1/10 to 2/1) to give (S)-7,8-dimethoxy-N-methyl-N-(tetrahydrofuran-3-yl)quinazolin-4-amine 410 mg (93%) as a white solid.

LC-MS (m/z) 290.1 (MH+), $t_R$ (minutes, method 6)=1.767.
$[\alpha]^{20}_D$=−21 (c=0.1 mg/mL, CHCl$_3$)

Example 5

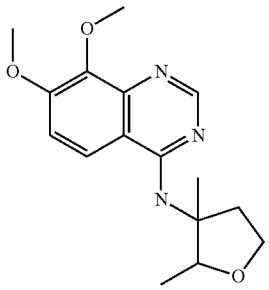 [SMILES: COc1ccc2c(NC3(C)CCOC3C)ncnc2c1OC]

N-(2,3-dimethyltetrahydrofuran-3-yl)-7,8-dimethoxyquinazolin-4-amine

A mixture of 4-chloro-7,8-dimethoxyquinazoline (8.4 g, 37 mmol), 2,3-dimethyltetrahydrofuran-3-amine (4.0 g, 35 mmol) and NaHCO$_3$ (2.6 g, 31 mmol) in DMSO (120 mL) was stirred at 100° C. for 12 hours. The solution was poured into ice-water (200 mL), extracted with DCM (3×100 mL). The combined organic phases were washed with brine (3×10 mL), dried over Na$_2$SO$_4$ and concentrated in vacuo. The residue was purified by flash chromatography on silica gel using a gradient of ethyl acetate and petroleum ether to give N-(2,3-dimethyltetrahydrofuran-3-yl)-7,8-dimethoxyquinazolin-4-amine 4.0 g (43%) as a white solid.

A mixture of all possible stereoisomers of N-(2,3-dimethyltetrahydrofuran-3-yl)-7,8-dimethoxyquinazolin-4-amine 6.0 g was purified by SFC separation and numbered according to their order of elution:

Stereoisomer 1 (first eluting by SFC): 536 mg,
LC-MS (m/z) 304.1 (MH+) $t_R$ (minutes, method 3)=1.98.
$[\alpha]^{20}_D=25$ (c=0.10 mg/mL, MeOH)

Stereoisomer 2 (second eluting by SFC): 546 mg,
LC-MS (m/z) 304.1 (MH+) $t_R$ (minutes, method 3)=1.98.
$[\alpha]^{20}_D=-14$ (c=0.10 mg/mL, MeOH)

Stereoisomer 3 (third eluting by SFC): 920 mg,
LC-MS (m/z) 304.1 (MH+) $t_R$ (minutes, method 3)=2.00.
$[\alpha]^{20}_D=22$ (c=0.10 mg/mL, MeOH)

Stereoisomer 4 (fourth eluting by SFC): 999 mg,
LC-MS (m/z) 304.1 (MH+) $t_R$ (minutes, method 3)=2.00.
$[\alpha]^{20}_D=-20$ (c=0.1 mg/mL, MeOH)

Example 6

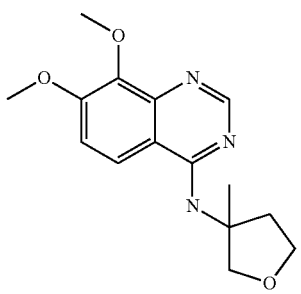 [SMILES: COc1ccc2c(NC3(C)CCOC3)ncnc2c1OC]

7,8-Dimethoxy-N-(3-methyltetrahydrofuran-3-yl)quinazolin-4-amine

4-Chloro-7,8-dimethoxyquinazoline (200 mg, 0.890 mmol) and 3-methyltetrahydrofuran-3-amine (90 mg, 0.890 mmol) were mixed in isopropanol (10 mL) and DIPEA (345 mg, 466 μl, 2.67 mmol). The reaction was heated for 2 hours at 170° C. in a microwave oven. Conversion not complete as judged by LCMS. 3-Methyltetrahydrofuran-3-amine (90 mg, 0.89 mmol) was then added and mixture heated for 40 min at 170° C. in a microwave oven. The reaction mixture was poured into H$_2$O (20 mL) and extracted with ethyl acetate (3×20 mL). The combined organic phases were washed with brine, dried over MgSO$_4$ and concentrated in vacuo. The crude product was purified by flash chromatography using a gradient of ethyl acetate and heptane yielding 7,8-dimethoxy-N-(3-methyltetrahydrofuran-3-yl)quinazolin-4-amine 63 mg, (23%).

LC-MS (m/z) 290.2 (MH+), $t_R$ (minutes, method 2)=0.33.

7,8-Dimethoxy-N-(3-methyltetrahydrofuran-3-yl)quinazolin-4-amine (900 mg, 0.35 mmol) was purified by SFC separation The pure fractions were collected and solvent was evaporated under vacuum to afford Stereoisomer 1 (First Eluting by SFC): 400 mg (44%).
LC-MS (m/z) 290.1 (MH+), $t_R$ (minutes, method 3)=1.945, ee %=98.9%.
$[\alpha]^{20}_D=11.67$ (c=0.1 mg/mL, MeOH)

Stereoisomer 2 (Second Eluting by SFC): 400 mg (44%).
LC-MS (m/z) 290.1 (MH+), $t_R$ (minutes, method 3)=1.951, ee %=97.7%.
$[\alpha]^{20}_D=-12.00$ (c=0.1 mg/mL, MeOH)

Example 7

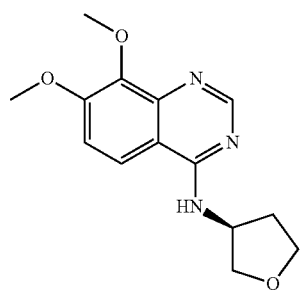 [SMILES: COc1ccc2c(N[C@H]3CCOC3)ncnc2c1OC]

(S)-7,8-Dimethoxy-N-(tetrahydrofuran-3-yl)quinazolin-4-amine

A solution of 4-chloro-7,8-dimethoxyquinazoline (1.5 g, 6.7 mmol), (S)-tetrahydrofuran-3-amine hydrochloride (1.00 g, 8.00 mmol) and DIPEA (3.44 g, 26.7 mmol) in DMF (20 mL) was stirred at 100° C. for 3 hours. The solution was concentrated under vacuum. The residue was diluted with DCM (300 mL) and washed with brine (3×50 mL). The organic layer was evaporated and the residue was purified by prep-HPLC to afford (S)-7,8-dimethoxy-N-(tetrahydrofuran-3-yl)quinazolin-4-amine 1.2 g (67%) as a white solid

Example 8

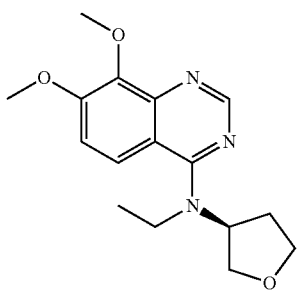 [SMILES: CCN(c1ncnc2c(OC)c(OC)ccc12)[C@H]1CCOC1]

(S)-N-ethyl-7,8-dimethoxy-N-(tetrahydrofuran-3-yl)
quinazon-4-amine

To a solution of (S)-7,8-dimethoxy-N-(tetrahydrofuran-3-yl)quinazolin-4-amine (200 mg, 0.73 mmol) in THF (2 mL) was added NaH (60%, 58 mg, 2.4 mmol) at 0° C., then it was stirred at 0° C. for 10 min. Iodoethane (135 mg, 0.87 mmol) was added at 0° C. and the reaction was warmed to 20° C. and stirred 12 hours. The solution was quenched with sat. aq. NH$_4$Cl (0.3 mL), and concentrated under vacuum. The residue was diluted with ethylacetate (50 mL), washed with brine, dried and concentrated under vacuum. The residue was purified by flash chromatography on silica gel (eluted ethylacetate/petroleum ether=1/10 to 2/1) to give the (S)-N-ethyl-7,8-dimethoxy-N-(tetrahydrofuran-3-yl)quinazolin-4-amine 58 mg (26%) as a white solid.

LC-MS (m/z) 304.2 (MH+), t$_R$ (minutes, method 3)=1.984.

Example 9

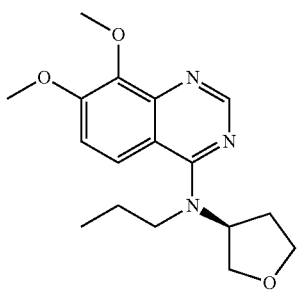 [SMILES: CCCN(c1ncnc2c(OC)c(OC)ccc12)[C@H]1CCOC1]

(S)-7,8-dimethoxy-N-propyl-N-(tetrahydrofuran-3-yl)quinazolin-4-amine

To a solution of (S)-7,8-dimethoxy-N-(tetrahydrofuran-3-yl)quinazolin-4-amine (200 mg, 0.73 mmol) in THF (2 mL) was added NaH (60%, 58 mg, 2.4 mmol) at 0° C., it was stirred at 0° C. for 10 min. 1-Iodopropane (148 mg, 0.87 mmol) was added to the reaction mixture at 0° C., then it was stirred at 20° C. for 12 hours. The reaction was quenched with sat. aq. NH$_4$Cl (0.3 mL), and concentrated under vacuum. The residue was diluted with ethyl acetate (50 mL), washed with brine, dried and concentrated under vacuum. The residue was purified by preparative LC-MS to give (S)-7,8-dimethoxy-N-propyl-N-(tetrahydrofuran-3-yl)quinazolin-4-amine 40 mg (17%) as a white solid.

LC-MS (m/z) 318.2 (MH+), t$_R$ (minutes, method 3)=2.176.

Example 10

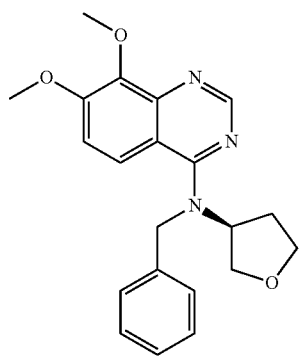 [SMILES: COc1ccc2c(N(Cc3ccccc3)[C@H]3CCOC3)ncnc2c1OC]

(S)-N-benzyl-7,8-dimethoxy-N-(tetrahydrofuran-3-yl)quinazolin-4-amine

To a solution of (S)-7,8-dimethoxy-N-(tetrahydrofuran-3-yl)quinazolin-4-amine (200 mg, 0.73 mmol) in THF (2 mL) was added NaH (58 mg, 2.4 mmol, 60%) at 0° C., then it was stirred at 0° C. for 10 min. benzylbromide (150 mg, 0.87 mmol) was added at 0° C., then it was stirred at 20° C. for 12 hours. The reaction was quenched with sat. aq. NH$_4$Cl (0.3 mL), and concentrated under vacuum. The residue was diluted with EA (50 mL), washed with brine, dried and concentrated under vacuum. The residue was purified by flash chromatography on silica gel using a gradient of ethyl acetate and heptane to give the (S)-N-benzyl-7,8-dimethoxy-N-(tetrahydrofuran-3-yl)quinazolin-4-amine 60 mg (23%) as a white solid.

LC-MS (m/z) 366.2 (MH+), t$_R$ (minutes, method 4)=1.640.

Example 11

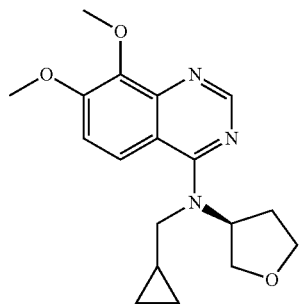 [SMILES: COc1ccc2c(N(CC3CC3)[C@H]3CCOC3)ncnc2c1OC]

(S)-N-(cyclopropylmethyl)-7,8-dimethoxy-N-(tetrahydrofuran-3-yl)quinazolin-4-amine To a solution of (S)-7,8-dimethoxy-N-(tetrahydrofuran-3-yl)quinazolin-4-amine (100 mg, 0.36 mmol) in DMF (3 mL) was added NaH (100 mg, 2.5 mmol, 60%) at 0° C., then it was stirred at 0° C. for 20 min. (bromomethyl)cyclopropane (58 mg, 0.44 mmol) was added at 0° C., then it was stirred at 20° C. for 12 hours. The reaction was quenched with sat. aq. NH₄Cl (0.3 mL), and concentrated under vacuum. The residue was diluted with ethyl acetate (50 mL), washed with brine, dried and concentrated under vacuum. The residue was purified by preparative LC-MS to give the (S)-N-(cyclopropylmethyl)-7,8-dimethoxy-N-(tetrahydrofuran-3-yl)quinazolin-4-amine 30 mg, (25%) as a white solid.

LC-MS (m/z) 330.0 (MH+), $t_R$ (minutes, method 3)=1.834.

Example 12

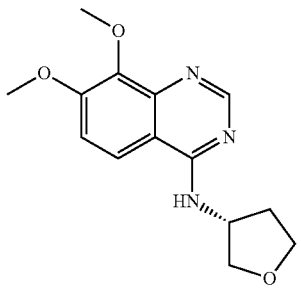 [SMILES: COc1ccc2c(N[C@@H]3CCOC3)ncnc2c1OC]

(R)-7,8-dimethoxy-N-(tetrahydrofuran-3-yl)quinazolin-4-amine

A solution of 4-chloro-7,8-dimethoxyquinazoline (1.5 g, 6.7 mmol), (R)-tetrahydrofuran-3-amine hydrochloride (1.00 g, 8.00 mmol) and DIPEA (3.44 g, 26.7 mmol) in DMF (20 mL) was stirred at 100° C. for 3 hours. The solution was concentrated under vacuum. The residue was diluted with DCM (300 mL) washed with brine (3×50 mL). The combined organic phases were evaporated and the residue was purified by prep-HPLC to afford (R)-7,8-dimethoxy-N-(tetrahydrofuran-3-yl)quinazolin-4-amine 1.2 g (67%) as a white solid Example 13

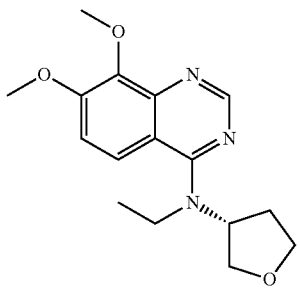 [SMILES: CCN(c1ncnc2c(OC)c(OC)ccc12)[C@@H]1CCOC1]

(R)-N-ethyl-7,8-dimethoxy-N-(tetrahydrofuran-3-yl)quinazolin-4-amine

To a solution of (R)-7,8-dimethoxy-N-(tetrahydrofuran-3-yl)quinazolin-4-amine (100 mg, 0.36 mmol) in THF (5 mL) was added NaH 60% (44 mg, 1.82 mmol) at 0° C., then stirred at 0° C. for 10 min. To the solution was added iodoethane (283 mg, 1.82 mmol) at 0° C., then stirred at 20° C. for 12 hours. The solution was quenched with sat. aq. NH₄Cl (0.3 mL), and concentrated under vacuum. The residue was diluted with ethyl acetate (50 mL), washed with brine, dried over MgSO₄ and concentrated under vacuum. The residue was purified by flash chromatography on silica gel (eluent: ethyl acetate/petroleum ether=1/10 to 2/1) to give the (R)-N-ethyl-7,8-dimethoxy-N-(tetrahydrofuran-3-yl)quinazolin-4-amine 36 mg (32%) as a white solid.

LC-MS (m/z) 304.1 (MH+), $t_R$ (minutes, method 5)=1.720.

Example 14

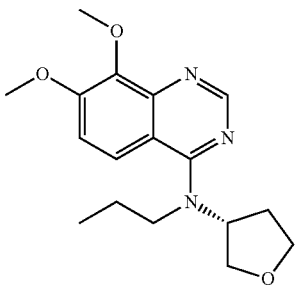 [SMILES: CCCN(c1ncnc2c(OC)c(OC)ccc12)[C@@H]1CCOC1]

(R)-7,8-dimethoxy-N-propyl-N-(tetrahydrofuran-3-yl)quinazolin-4-amine

To a solution of (R)-7,8-dimethoxy-N-(tetrahydrofuran-3-yl)quinazolin-4-amine (100 mg, 0.36 mmol) in THF (5 mL) was added NaH 60% (44 mg, 1.82 mmol) at 0° C., then stirred at 0° C. for 10 min. Then 1-iodopropane (309 mg, 1.82 mmol) was added to the solution at 0° C., the reaction was stirred at 20° C. for 12 hours. The solution was quenched with sat. aq. NH₄Cl (0.3 mL), and concentrated under vacuum. The residue was diluted with ethyl acetate (50 mL), washed with brine, dried over MgSO₄ and concentrated under vacuum. The residue was purified by flash chromatography on silica gel (eluent ethyl acetate/petroleum ether-=1/10 to 2/1) to give (R)-7,8-dimethoxy-N-propyl-N-(tetrahydrofuran-3-yl)quinazolin-4-amine 41 mg (35%) as a white solid.

LC-MS (m/z) 318.1 (MH+), $t_R$ (minutes, method 3)=1.779.

Example 15

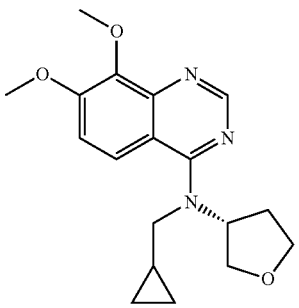 [SMILES: COc1ccc2c(N(CC3CC3)[C@@H]3CCOC3)ncnc2c1OC]

(R)-N-(cyclopropylmethyl)-7,8-dimethoxy-N-(tetra-hydrofuran-3-yl)quinazolin-4-amine To a solution of (R)-7,8-dimethoxy-N-(tetrahydrofuran-3-yl)quinazolin-4-amine (100 mg, 0.36 mmol) in DMF (5 mL) was added NaH 60% (44 mg, 1.82 mmol) at 0° C., then stirred at 0° C. for 20 min. Then (bromomethyl)cyclopropane (246 mg, 1.82 mmol) was added to the solution at 0° C., then stirred at 20° C. for 12 hours. The solution was quenched with sat. aq. NH$_4$Cl (0.3 mL), and concentrated under vacuum. The residue was diluted with ethyl acetate (50 mL), washed with brine, dried over MgSO$_4$ and concentrated under vacuum. The residue was purified prep-HPLC to give (R)-N-(cyclopropylmethyl)-7,8-dimethoxy-N-(tetrahydrofuran-3-yl)quinazolin-4-amine 36 mg (32%) as a white solid.

LC-MS (m/z) 330.1 (MH+), $t_R$ (minutes, method 3)=1.816.

Example 16

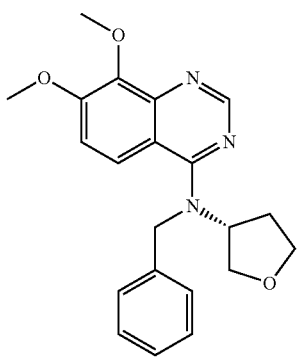 [SMILES: COc1ccc2c(N(Cc3ccccc3)[C@@H]3CCOC3)ncnc2c1OC]

(R)-N-benzyl-7,8-dimethoxy-N-(tetrahydrofuran-3-yl)quinazolin-4-amine

To a solution of (R)-7,8-dimethoxy-N-(tetrahydrofuran-3-yl)quinazolin-4-amine (100 mg, 0.36 mmol) in THF (5 mL) was added NaH 60% (73 mg, 1.82 mmol) at 0° C., then stirred at 0° C. for 10 min. Then benzylbromide (311 mg, 1.82 mmol) was added to the solution at 0° C., then stirred at 20° C. for 12 hours. The solution was quenched with sat. aq. NH$_4$Cl (0.3 mL), and concentrated under vacuum. The residue was diluted with ethyl acetate (50 mL), washed with brine, dried over MgSO$_4$ and concentrated under vacuum. The residue was purified by flash chromatography on silica gel (eluent: ethyl acetate/petroleum ether=1/10 to 1/1) to give (R)-N-benzyl-7,8-dimethoxy-N-(tetrahydrofuran-3-yl)quinazolin-4-amine 52 mg (45%) as a white solid.

LC-MS (m/z) 366.2 (MH+), $t_R$ (minutes, method 4)=1.705.

Example 17

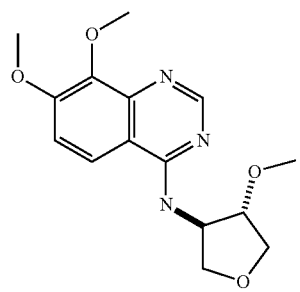

Trans-7,8-dimethoxy-N-(4-methoxytetrahydrofuran-3-yl)quinazolin-4-amine

4-Chloro-7,8-dimethoxyquinazoline (200 mg, 0.890 mmol) and trans-4-methoxytetrahydrofuran-3-amine hydrochloride (164 mg, 1.07 mmol) were mixed in isopropanol (4 mL) and DIPEA (1270 µl, 7.27 mmol). The reaction was heated for 40 min at 160° C. under microwave irradiation. The reaction was poured into H$_2$O (25 mL) and extracted with ethyl acetate (3×25 mL), the combined org. phases were washed with brine, dried over MgSO4 and concentrated in vacuo. Purified by flashchromatography using a gradient of heptane and ethyl acetate to yield trans-7,8-dimethoxy-N-4-methoxytetrahydrofuran-3-yl)quinazolin-4-amine (220 mg, 0.721 mmol, 81% yield).

LC-MS (m/z) 306.2 (MH+), $t_R$ (minutes, method 2)=0.37.

Example 18

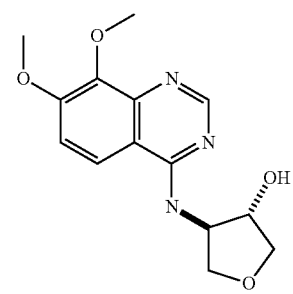

trans-4-((7,8-dimethoxyquinazolin-4-yl)amino)tetrahydrofuran-3-ol

4-Chloro-7,8-dimethoxyquinazoline (200 mg, 0.890 mmol) and 4-amino-tetrahydrofuran-3-ol hydrochloride (149 mg, 1.068 mmol) were mixed in isopropanol (3.6 mL) and DIPEA (1270 µl, 7.27 mmol). The mixture was heated in microwave oven for 40 min at 160° C. The reaction was cooled to RT overnight, and the precipitate was isolated by filtration to yield trans-4-((7,8-dimethoxyquinazolin-4-yl)amino)tetrahydrofuran-3-ol 214 mg (83% yield)

LC-MS (m/z) 292.1 (MH+), $t_R$ (minutes, method 2)=0.31.

Example 19

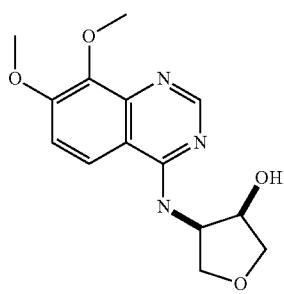

cis-4-((7,8-dimethoxyquinazolin-4-yl)amino)tetrahydrofuran-3-ol

4-Chloro-7,8-dimethoxyquinazoline (200 mg, 0.890 mmol) and cis-4-amino-tetrahydrofuran-3-ol hydrochloride (149 mg, 1.07 mmol) were mixed in isopropanol (3.6 mL) and DIPEA (1270 µl, 7.27 mmol). The mixture was heated for 40 min at 160° C. in microwave oven. Cooled to RT and the solid precipitate was filtered of to yield cis-4-((7,8-dimethoxyquinazolin-4-yl)amino)tetrahydrofuran-3-ol 224 mg (86%).

LC-MS (m/z) 292.1 (MH+), $t_R$ (minutes, method 2)=0.31.

Example 20

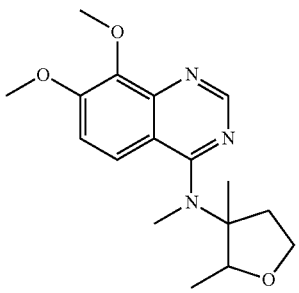 [SMILES: COc1ccc2c(N(C)C3(C)CCOC3C)ncnc2c1OC]

N-(2,3-dimethyltetrahydrofuran-3-yl)-7,8-dimethoxy-N-methylquinazolin-4-amine

To an ice-cold solution of N-(2,3-dimethyltetrahydrofuran-3-yl)-7,8-dimethoxy-quinazolin-4-amine (example 5) (800 mg, 2.64 mmol), in THF (50 mL) was added NaH (160 mg, 3.97 mmol, 60% in mineral oil). The mixture was allowed to warm to 20° C. and stirred for 30 min. MeI (560 mg, 3.97 mmol) was added and the reaction was stirred for a further 3 hrs. The solution was quenched with sat. NH$_4$Cl (aq. 2 mL) at 0 5° C., and concentrated under vacuum. The residue was diluted with DCM (50 mL), washed with brine (3×5 mL), dried and concentrated under vacuum. The residue was purified by flash chromatography on silica gel using a gradient of ethyl acetate and petroleum ether to give the N-(2,3-dimethyltetrahydrofuran-3-yl)-7,8-dimethoxy-N-methylquinazolin-4-amine 580 mg (69%).

N-(2,3-Dimethyltetrahydrofuran-3-yl)-7,8-dimethoxy-N-methylquinazolin-4-amine 580 mg was purified by preparative-TLC (ethyl acetate/petroleum ether=2/1) to give racemic diastereomer 1 300 mg, (52%), and racemic diastereomer 2, 240 mg, (41%).

The racemate of diastereomer 1 (300 mg) was purified by SFC to afford:

Stereoisomer 1 (first eluting by SFC): 120 mg, (40%)
$^1$H NMR (CDCl$_3$ varian 400): δ 8.76 (s, 1H), 7.71 (d, J=4.6 Hz, 1H), 7.21 (d, J=4.6 Hz, 1H), 4.39-4.36 (m, 1H), 4.09 (s, 3H), 4.03 (s, 3H), 3.92-3.89 (m, 1H), 3.85-3.81 (m, 1H), 3.22 (s, 3H), 2.56-2.49 (m, 1H), 2.31-2.23 (m, 1H), 1.60 (s, 3H), 1.37 (d, J=3.2 Hz, 3H).
LC-MS (m/z) 318.2 (MH+) $t_R$ (minutes, method 3)=2.01.
$[α]_D^{20}$ −35 (c=0.10, MeOH).

Stereoisomer 2 (second eluting by SFC): 120 mg, (40%).
$^1$H NMR (CDCl$_3$ varian 400): δ 8.75 (s, 1H), 7.71 (d, J=4.6 Hz, 1H), 7.21 (d, J=4.6 Hz, 1H), 4.39-4.35 (m, 1H), 4.08 (s, 3H), 4.03 (s, 3H), 3.92-3.89 (m, 1H), 3.85-3.81 (m, 1H), 3.19 (s, 3H), 2.55-2.49 (m, 1H), 2.31-2.23 (m, 1H), 1.61 (s, 3H), 1.37 (d, J=3.0 Hz, 3H).
LC-MS (m/z) 318.2 (MH+) $t_R$ (minutes, method 3)=2.00.
$[α]_D^{20}$ +40 (c=0.10, MeOH).

The racemate of diastereomer 2 (240 mg) was purified by SFC to afford:

Stereoisomer 3 (first eluting by SFC): 100 mg (42%),
$^1$H NMR (CDCl$_3$ varian 400): δ 8.67 (s, 1H), 7.71 (d, J=4.8 Hz, 1H), 7.18 (d, J=4.8 Hz, 1H), 4.80-4.79 (m, 1H), 4.09 (s, 3H), 4.02 (s, 3H), 4.05-4.02 (m, 1H), 3.94-3.87 (m, 1H), 3.28 (s, 3H), 2.46-2.38 (m, 1H), 2.18-2.14 (m, 1H), 1.72 (s, 3H), 0.95 (d, J=3.2 Hz, 3H).
LC-MS (m/z) 318.2 (MH+) $t_R$ (minutes, method 3)=1.99.
$[α]_D^{20}$ +10 (c=0.10, MeOH).

Stereoisomer 4 (second eluting by SFC): 100 mg, (42%),
$^1$H NMR (CDCl$_3$ varian 400): δ 8.70 (s, 1H), 7.71 (d, J=4.8 Hz, 1H), 7.19 (d, J=4.8 Hz, 1H), 4.83-4.78 (m, 1H), 4.09 (s, 3H), 4.02 (s, 3H), 4.06-4.02 (m, 1H), 3.94-3.87 (m, 1H), 3.30 (s, 3H), 2.47-2.39 (m, 1H), 2.18-2.14 (m, 1H), 1.71 (s, 3H), 0.95 (d, J 15=3 Hz, 3H).
LC-MS (m/z) 318.2 (MH+) $t_R$ (minutes, method 3)=1.99.
$[α]_D^{20}$ −10 (c=0.10, MeOH).

Example 21

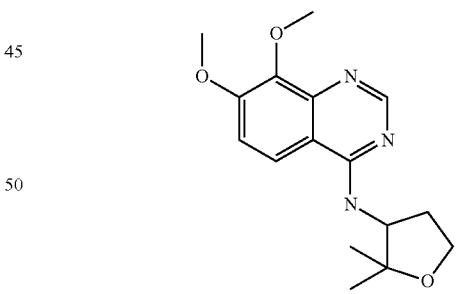

N-(2,2-dimethyltetrahydrofuran-3-yl)-7,8-dimethoxyquinazolin-4-amine

Step 1:
To a solution of methyl 2-hydroxy-2-methylpropanoate (10 g, 185 mmol) in THF (120 mL) was added NaH 60% in mineral oil (3.4 g, 84.7 mmol) at 0° C. The mixture was allowed to warm to 20° C. and stirred for 30 minutes. The solvent was removed under vacuum. A solution of methyl acrylate (8.0 g, 93 mmol) in DMSO (100 mL) was added. The mixture was stirred at 20° C. for 30 minutes. A 6 M solution HCl (80 mL) was added. The mixture was extracted with MTBE (3×50 mL). The organic layer was washed with sat. aqueous NaHCO₃ (40 mL), then brine (40 mL), dried over Na₂SO₄ and evaporated under vacuum. The crude product of methyl 5,5-dimethyl-4-oxotetrahydrofuran-3-carboxylate (12 g) was used directly for step 2 without further purification.

Step 2:
Methyl 5,5-dimethyl-4-oxotetrahydrofuran-3-carboxylate (5.0 g, 29 mmol) was dissolved in 12N HCl (30 mL). The mixture was stirred at 100° C. for 2 hours. Then allowed to cool to rt and pH was adjusted to pH 8 with sat. aqueous NaHCO₃ and extracted with MTBE (3×30 mL). The combined organic phases were washed with water (2×30 mL), dried over Na₂SO₄ and evaporated under vacuum. The crude product of 2,2-dimethyldihydrofuran-3(2H)-one (1.1 g) was used in the next step.

Step 3:
2,2-Dimethyldihydrofuran-3(2H)-one (1.0 g, 8.8 mmol) and 2-methylpropane-2-sulfinamide (1.1 g, 8.8 mmol) were dissolved in THF (30 mL). Ti(i-PrO)₄ (2.9 g, 10 mmol) was added. The mixture was stirred at 60° C. for 8 hours. The mixture was diluted with ethyl acetate (100 mL) and washed with water (2×50 mL). The organic layer was dried over Na₂SO₄ and evaporated under vacuum. The residue was purified by silica gel chromatography using a gradient of petroleum ether and ethyl acetate to give N-(2,2-dimethyl-dihydrofuran-3(2H)-ylidene)-2-methylpropane-2-sulfinamide 900 mg (47%).

Step 4:
N-(2,2-dimethyldihydrofuran-3(2H)-ylidene)-2-methylpropane-2-sulfinamide (900 mg, 4.1 mmol) was dissolved in THF (30 mL). NaBH₄ (310 mg, 8.2 mmol) was added at 0° C. The reaction was then stirred at 20° C. for 1 hr. The mixture was quenched with aqueous sat. NH₄Cl (0.5 mL) and diluted with ethyl acetate (100 mL) and washed with water (30 mL). The organic phase was dried over Na₂SO₄ and evaporated under vacuum. The crude product (700 mg) was used directly in the next step.

Step 5:
N-(2,2-dimethyltetrahydrofuran-3-yl)-2-methylpropane-2-sulfinamide (400 mg, 1.80 mmol) was dissolved in 12 M HCl (80 mL). The mixture was stirred at 50° C. for 2 hrs. The reaction was basified with sat. aqueous NaHCO₃ to pH=8 and extracted with DCM (3×10 mL). The combined organic phases were washed with water (2×10 mL), dried over Na₂SO₄ and evaporated under vacuum. The crude product of 2,2-dimethyltetrahydrofuran-3-amine (209 mg) was used directly in the next step.

Step 6:
A mixture of 2,2-dimethyltetrahydrofuran-3-amine (209 mg, 1.80 mmol), 4-chloro-7,8-dimethoxyquinazoline (500 mg, 1.80 mmol) and DIPEA (470 mg, 3.60 mmol) in DMF (15 mL) was stirred at 100° C. for 1 hr. The solvent was removed under vacuum. And the residue was dissolved in DCM (50 mL) and washed with water (3×15 mL). The organic phase was dried over Na₂SO₄ and evaporated under vacuum. The residue was purified by silica gel chromatography using a gradient of DCM and MeOH to give N-(2,2-dimethyltetrahydrofuran-3-yl)-7,8-dimethoxyquinazolin-4-amine 75 mg (13%).

The racemate of N-(2,2-dimethyltetrahydrofuran-3-yl)-7,8-dimethoxyquinazolin-4-amine 75 mg was purified by SFC separation and numbered according to their order of elution:

Stereoisomer 1 (first eluting by SFC): 30 mg (40%)
LC-MS (m/z) 304.2 (MH+) $t_R$ (minutes, method 3)=1.95.
$[\alpha]_D^{20}$−74 (c=0.10, MeOH).

Stereoisomer 2 (second eluting by SFC): 30 mg (40%)
LC-MS (m/z) 304.2 (MH+) $t_R$ (minutes, method 3)=1.95.
$[\alpha]_D^{20}$+67 (c=0.10, MeOH).

Example 22

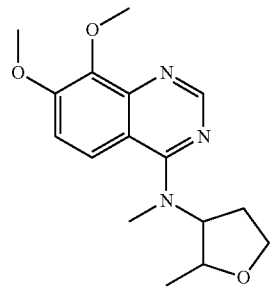 [SMILES: COc1ccc2c(N(C)C3CCOC3C)ncnc2c1OC]

7,8-dimethoxy-N-methyl-N-(2-methyltetrahydro-furan-3-yl)quinazolin-4-amine

Step 1:
To a solution of 2-methyltetrahydrofuran-3-amine hydrochloride (mixture of all four possible stereoisomers) (600 mg, 4.34 mmol) in DMF (10 mL) was added 4-chloro-7,8-dimethoxyquinazoline (650 mg, 2.89 mmol) and DIPEA (1.2 g, 9.3 mmol). The reaction was stirred overnight at 100° C. The reaction mixture was concentrated in vacuo and the residue was diluted with DCM (100 mL), washed with sat. NaHCO₃ (aq), then brine, dried over Na₂SO₄ and concentrated in vacuo. The residue was purified by silica gel chromatography (DCM:MeOH=10:1) to afford 700 mg of 7,8-dimethoxy-N-(2-methyltetrahydrofuran-3-yl)quinazolin-4-amine (84%).

Step 2:
A solution of 7,8-dimethoxy-N-(2-methyltetrahydrofuran-3-yl)quinazolin-4-amine (750 mg, 2.59 mmol) in DMF/THF (2 mL/10 mL) was cooled to 0° C. NaH (207 mg, 5.18 mmol, 60% in mineral oil) was added. The mixture was stirred at 0° C. for 10 min. Then MeI (736 mg, 5.18 mmol) was added. After the addition, the mixture was allowed to warm to rt and stirred for 1 h. The mixture was quenched with sat. NH₄Cl (aq), extracted with DCM (2×50 mL). The combined organic phases were washed with brine, dried over Na₂SO₄ and concentrated. The residue purified by preparative-HPLC to afford 250 mg of 7,8-dimethoxy-N-methyl-N-(2-methyltetrahydrofuran-3-yl)quinazolin-4-amine (32%).

The mixture of all possible stereoisomers of 7,8-dimethoxy-N-methyl-N-(2-methyltetrahydrofuran-3-yl)quinazolin-4-amine 280 mg was purified by SFC separation twice. The first run separated the two racemic diastereomers. Each of these racemates were then subjected to another SFC-purification and separated into enantiomers.

Stereoisomers 1: 55 mg
¹H NMR (CDCl₃ 400 MHz): δ 8.64 (s, 1H), 7.76 (d, J=9.2 Hz, 1H), 7.13 (d, J=9.2 Hz, 1H), 5.42 (brs, 1H), 4.20-4.14 (m, 1H), 4.07-4.01 (m, 7H), 3.74-3.71 (m, 1H), 3.36 (s, 3H), 2.44-2.39 (m, 1H), 2.30-2.28 (m, 1H), 1.28 (d, J=6.4 Hz, 3H).
LC-MS (m/z) 304.1 (MH+) $t_R$ (minutes, method 3)=1.57.
$[\alpha]_D^{20}$−47 (c=0.10, MeOH).

Stereoisomer 2: 17 mg

¹H NMR (CDCl₃ 400 MHz): δ 8.67 (s, 1H), 7.71 (d, J=9.2 Hz, 1H), 7.12 (d, J=9.2 Hz, 1H), 4.87 (brs, 1H), 4.15-4.08 (m, 1H), 4.03-3.96 (m, 8H), 3.29 (s, 3H), 2.50-2.43 (m, 1H), 2.10-2.03 (m, 1H), 1.23 (d, J=6.4 Hz, 3H).

LC-MS (m/z) 304.1 (MH+) $t_R$ (minutes, method 3)=1.56. $[α]_D^{20}$+17 (c=0.10, MeOH).

Stereoisomer 3: 45 mg

¹H NMR (CDCl₃ 400 MHz): δ 8.70 (s, 1H), 7.75 (d, J=9.2 Hz, 1H), 7.17 (d, J=9.2 Hz, 1H), 4.83 (brs, 1H), 4.20-4.14 (m, 1H), 4.08-4.01 (m, 8H), 3.30 (s, 3H), 2.55-2.47 (m, 1H), 2.16-2.07 (m, 1H), 1.28 (d, J=6.0 Hz, 3H).

LC-MS (m/z) 304.1 (MH+) $t_R$ (minutes, method 3)=1.57. $[α]_D^{20}$-17 (c=0.10, MeOH).

Stereoisomer 4: 25 mg

¹H NMR (CDCl₃ 400 MHz): δ 8.58 (s, 1H), 7.71 (d, J=9.2 Hz, 1H), 7.07 (d, J=9.2 Hz, 1H), 5.34-5.33 (m, 1H), 4.13-4.09 (m, 1H), 4.01-3.95 (m, 7H), 3.68-3.65 (m, 1H), 3.30 (s, 3H), 2.38-2.34 (m, 1H), 2.25-2.22 (m, 1H), 1.23 (d, J=6.4 Hz, 3H).

LC-MS (m/z) 304.1 (MH+) $t_R$ (minutes, method 3)=1.57. $[α]_D^{20}$+56 (c=0.10, MeOH).

Example 23

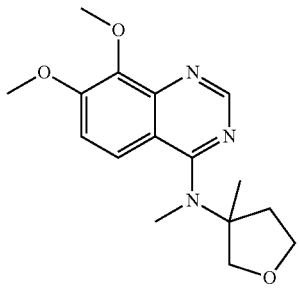 [SMILES: COc1ccc2c(N(C)C3(C)CCOC3)ncnc2c1OC]

7,8-Dimethoxy-N-methyl-N-(3-methyltetrahydrofuran-3-yl)quinazolin-4-amine

To an ice-cold solution of 7,8-dimethoxy-N-(3-methyltetrahydrofuran-3-yl)quinazolin-4-amine (300 mg, 1.03 mmol) in THF (15 mL) was added NaH (60% in mineral oil) (60 mg, 1.5 mmol) at 0° C. and it was then allowed to RT. After stirring at rt for 30 min. MeI (211 mg, 1.5 mmol) was added. Stirring was continued for 3 hrs. The solution was quenched by addition of sat. NH₄Cl (aq. 1 mL), and subsequently concentrated under vacuum. The residue was diluted with DCM (60 mL). The organic layer was washed with water, brine, dried over Na₂SO₄ and concentrated under vacuum. The residue was purified by flash chromatography silica gel using a gradient of ethyl acetate and petroleum ether to give 7,8-dimethoxy-N-methyl-N-(3-methyltetrahydrofuran-3-yl)quinazolin-4-amine 260 mg (86%).

The racemate of 7,8-dimethoxy-N-methyl-N-(3-methyltetrahydrofuran-3-yl)quinazolin-4-amine 260 mg was purified by SFC separation and numbered according to the order of elution:

Stereoisomer 1 (first eluting by SFC): 80 mg

LC-MS (m/z) 304.2 (MH+) $t_R$ (minutes, method 3)=1.81. $[α]_D^{20}$+15 (c=0.10, MeOH).

Stereoisomer 2 (second eluting by SFC): 74 mg

LC-MS (m/z) 304.2 (MH+) $t_R$ (minutes, method 3)=1.82. $[α]_D^{20}$-17 (c=0.10, MeOH).

Example 24

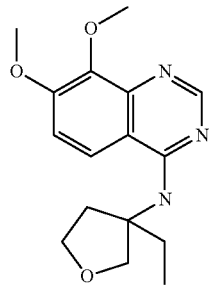 [SMILES: CCC1(Nc2ncnc3c(OC)c(OC)ccc23)CCOC1]

N-(3-Ethyltetrahydrofuran-3-yl)-7,8-dimethoxyquinazolin-4-amine

To a mixture of 4-chloro-7,8-dimethoxyquinazoline (100 mg, 0.445 mmol) and 3-ethyltetrahydrofuran-3-amine hydrochloride (68 mg, 0.45 mmol) in isopropanol (1.5 mL) was added DIPEA (144 mg, 1.1 mmol). The mixture was heated under microwave irradiation at 170° C. for 80 min. The reaction mixture was poured into H₂O (50 mL) and extracted with ethyl acetate (3×50 mL). The combined organic phases were washed with brine, dried over MgSO₄ and concentrated in vacuo. The mixture was purified by flash chromatography using a gradient of ethyl acetate and heptane to yield 54 mg N-(3-ethyltetrahydrofuran-3-yl)-7,8-dimethoxyquinazolin-4-amine (48%).

LC-MS (m/z) 304.2 (MH+) $t_R$ (minutes, method 2)=0.39.

Example 25

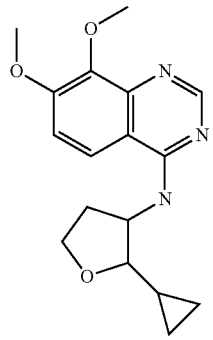 [SMILES: COc1ccc2c(NC3CCOC3C3CC3)ncnc2c1OC]

N-(2-Cyclopropyltetrahydrofuran-3-yl)-7,8-dimethoxyquinazolin-4-amine

To a mixture of 4-chloro-7,8-dimethoxyquinazoline (200 mg, 0.890 mmol) and 2-cyclopropyltetrahydrofuran-3-amine (170 mg, 1.34 mmol) in isopropanol (10 mL) was added DIPEA (0.311 ml, 1.78 mmol) and the reaction was heated under microwave irradiation at 160° C. for 40 min. After cooling to room temperature for 4 hours a white precipitate was collected and dried in vacuo at 40° C.

overnight to yield 80 mg of trans-N-(2-Cyclopropyltetrahydrofuran-3-yl)-7,8-dimethoxyquinazolin-4-amine (29%).

LC-MS (m/z) 316.0 (MH+) $t_R$ (minutes, method 2)=0.36.

Pde1 Inhibition Assay

PDE1A, PDE1B and PDE1C assays were performed as follows: the assays was performed in 60 μL samples containing a fixed amount of the PDE1 enzyml (sufficient to convert 20-25% of the cyclic nucleotide substrate), a buffer (50 mM HEPES pH 7.6; 10 mM $MgCl_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (PerkinElmer). The beads were allowed to settle for 1 h in the dark before the plates were counted in a Wallac 1450 Microbeta counter. The measured signals were converted to activity relative to an uninhibited control (100%) and $IC_{50}$ values were calculated using XlFit (model 205, IDBS).

What is claimed is:

1. A method of treating a neurodegenerative or psychiatric disorder, wherein said method comprises administering to a subject in need thereof, a therapeutically effective amount of:
   (A) a compound having the structure of Compound (I):

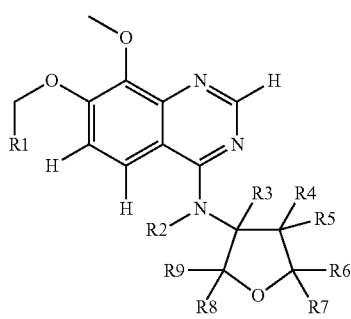

Compound (I)

wherein:
   $R_1$ is selected from the group consisting of H and $C_1$-$C_3$ alkyl;
   $R_2$ is selected from the group consisting of H and $C_1$-$C_3$ alkyl, wherein the $C_1$-$C_3$ alkyl optionally is substituted with phenyl or $C_3$-$C_6$ cycloalkyl;
   $R_3$ is selected from the group consisting of H, methyl and ethyl;
   $R_4$ is selected from the group consisting of H, hydroxyl, methoxy and ethoxy;
   $R_5$, $R_6$ and $R_7$ are H;
   $R_8$ is selected from the group consisting of H, methyl, ethyl and cyclopropyl; and
   $R_9$ is selected from the group consisting of H, methyl and ethyl;
or
   (B) a pharmaceutically acceptable acid addition salt of Compound (I), a racemic mixture of Compound (I), the corresponding enantiomer and/or optical isomer of Compound (I), a polymorphic form of Compound (I), or a tautomeric form of Compound (I);
wherein said neurodegenerative or psychiatric disorder is ADHD, schizophrenia or cognitive impairment associated with schizophrenia.

2. The method of claim 1, wherein said neurodegenerative or psychiatric disorder is ADHD.

3. The method of claim 1, wherein said neurodegenerative or psychiatric disorder is schizophrenia.

4. The method of claim 1, wherein said neurodegenerative or psychiatric disorder is cognitive impairment associated with schizophrenia.

5. The method according to claim 1, wherein $R_2$ of said Compound (I) is H.

6. The method according to claim 1, wherein $R_2$ of said Compound (I) is methyl.

7. The method according to claim 6, wherein $R_2$ of said Compound (I) is substituted with phenyl or cyclopropyl.

8. The method according to claim 1, wherein said Compound (I) is selected from the group consisting of:
   (1) 7,8-dimethoxy-N-(tetrahydrofuran-3-yl)quinazolin-4-amine;
   (2) trans-N-(-2-cyclopropyltetrahydrofuran-3-yl)-7,8-dimethoxyquinazolin-4-amine;
   (3) 7,8-dimethoxy-N-(-2-methyltetrahydrofuran-3-yl)quinazolin-4-amine;
   (4) 7,8-dimethoxy-N-methyl-N-(tetrahydrofuran-3-yl)quinazolin-4-amine;
   (5) (R)-7,8-dimethoxy-N-methyl-N-(tetrahydrofuran-3-yl)quinazolin-4-amine;
   (6) (S)-7,8-dimethoxy-N-methyl-N-(tetrahydrofuran-3-yl)quinazolin-4-amine;
   (7) N-(2,3-dimethyltetrahydrofuran-3-yl)-7,8-dimethoxy-quinazolin-4-amine;
   (8) 7,8-dimethoxy-N-(3-methyltetra-hydrofuran-3-yl)quinazolin-4-amine;
   (9) (S)-7,8-dimethoxy-N-(tetrahydrofuran-3-yl)quinazolin-4-amine;
   (10) (S)-N-ethyl-7,8-dimethoxy-N-(tetrahydrofuran-3-yl)quinazolin-4-amine;
   (11) (S)-7,8-dimethoxy-N-propyl-N-(tetrahydrofuran-3-yl)quinazolin-4-amine;
   (12) (S)-N-benzyl-7,8-dimethoxy-N-(tetrahydrofuran-3-yl)quinazolin-4-amine;
   (13) (S)-N-(cyclopropylmethyl)-7,8-dimethoxy-N-(tetrahydrofuran-3-yl)quinazolin-4-amine;
   (14) (R)-7,8-dimethoxy-N-(tetrahydrofuran-3-yl)quinazolin-4-amine;
   (15) (R)-N-ethyl-7,8-dimethoxy-N-(tetrahydrofuran-3-yl)quinazolin-4-amine;
   (16) (R)-7,8-dimethoxy-N-propyl-N-(tetrahydrofuran-3-yl)quinazolin-4-amine;
   (17) (R)-N-(cyclopropylmethyl)-7,8-dimethoxy-N-(tetrahydrofuran-3-yl)quinazolin-4-amine;
   (18) (R)-N-benzyl-7,8-dimethoxy-N-(tetrahydrofuran-3-yl)quinazolin-4-amine;
   (19) trans-7,8-dimethoxy-N-4-methoxytetrahydrofuran-3-yl)quinazolin-4-amine;
   (20) trans-4-((7,8-dimethoxyquinazolin-4-yl)amino)tetrahydrofuran-3-ol;
   (21) cis-4-((7,8-dimethoxyquinazolin-4-yl)amino)tetrahydrofuran-3-ol;
   (22) N-(2,3-dimethyltetrahydrofuran-3-yl)-'7,8-dimethoxy-N-methylquinazolin-4-amine;
   (23) N-(2,2-dimethyltetrahydrofuran-3-yl)-'7,8-dimethoxyquinazolin-4-amine;
   (24) 7,8-dimethoxy-N-methyl-N-(2-methyltetrahydrofuran-3-yl)quinazolin-4-amine;
   (25) 7,8-dimethoxy-N-methyl-N-(3-methyltetrahydrofuran-3-yl)quinazolin-4-amine;
   (26) N-(3-ethyltetrahydrofuran-3-yl)-'7,8-dimethoxyquinazolin-4-amine; and

(27) N-(2-cyclopropyltetrahydrofuran-3-yl)-'7,8-dimethoxyquinazolin-4-amine.

9. The method of claim 8, wherein said neurodegenerative or psychiatric disorder is ADHD.

10. The method of claim 8, wherein said neurodegenerative or psychiatric disorder is schizophrenia.

11. The method of claim 8, wherein said neurodegenerative or psychiatric disorder is cognitive impairment associated with schizophrenia.

* * * * *